(12) United States Patent
Hamamoto et al.

(10) Patent No.: US 11,903,939 B2
(45) Date of Patent: Feb. 20, 2024

(54) PATCH PREPARATIONS WITH ACCIDENTAL USE PREVENTION FEATURES

(71) Applicant: MEDRx Co., LTD, Higashikagawa (JP)

(72) Inventors: Hidetoshi Hamamoto, Higashikagawa (JP); Yasushi Miwa, Higashikagawa (JP); Katsuhiro Yamanaka, Higashikagawa (JP); Noboru Tatsumi, Higashikagawa (JP)

(73) Assignee: MEDRX CO., LTD., Kagawa (JP)

( * ) Notice: Subject to any disclaimer, the term of this patent is extended or adjusted under 35 U.S.C. 154(b) by 0 days.

(21) Appl. No.: 16/282,215

(22) Filed: Feb. 21, 2019

(65) Prior Publication Data

US 2019/0175585 A1 Jun. 13, 2019

Related U.S. Application Data

(63) Continuation of application No. 15/495,703, filed on Apr. 24, 2017, now abandoned, which is a
(Continued)

(30) Foreign Application Priority Data

Mar. 24, 2016 (JP) ................... 2016-060817

(51) Int. Cl.
*A61K 31/485* (2006.01)
*A61K 9/70* (2006.01)
(Continued)

(52) U.S. Cl.
CPC ...... *A61K 31/485* (2013.01); *A61F 13/00063* (2013.01); *A61F 13/023* (2013.01);
(Continued)

(58) Field of Classification Search
CPC .............. A61F 13/00063; A61F 13/023; A61F 13/0289; A61K 9/7084; A61K 31/4468; A61M 2205/273
See application file for complete search history.

(56) References Cited

U.S. PATENT DOCUMENTS 5,032,403 A * 7/1991 Sinnreich ............. A61K 9/7053
424/443
5,352,456 A 10/1994 Fallon et al.
(Continued)

FOREIGN PATENT DOCUMENTS

EP 2865376 4/2015
EP 3045166 7/2016
(Continued)

OTHER PUBLICATIONS

Hori et al., "Emhancement of Propranolol Hydrochloride and Diazepam Skin Adsorption In Vitro: Effect of Enhancer Lipophilicity", Journal of Pharmaceutical Sciences, vol. 80, No. 1, Jan. 1991. (Year: 1991).*

(Continued)

*Primary Examiner* — Jianfeng Song
(74) *Attorney, Agent, or Firm* — Morgan, Lewis & Bockius LLP

(57) ABSTRACT

The present disclosure provides a patch preparation having features that prevent accidental use. In some embodiments, a patch preparation containing a plaster on a support, wherein the plaster comprises a solvent that is a combination of ethyl acetate and n-heptane. The patch preparation can lose its adhesion after the plaster is exposed to air and at least some of the solvent has evaporated, or if the patch is removed from the skin. This feature prevent the used patch (Continued)

from being applied to the skin again, and can prevent accidental use. A method of forming a patch preparation is also disclosed.

16 Claims, 4 Drawing Sheets

Related U.S. Application Data continuation-in-part of application No. PCT/JP2017/010779, filed on Mar. 16, 2017.

(51) Int. Cl.
  *A61F 13/02* (2006.01)
  *A61F 13/00* (2006.01)
  *A61K 31/4468* (2006.01)
  *A61M 35/00* (2006.01)

(52) U.S. Cl.
  CPC ........ *A61F 13/0289* (2013.01); *A61K 9/7084* (2013.01); *A61K 31/4468* (2013.01); *A61M 2205/273* (2013.01)

(56) References Cited

U.S. PATENT DOCUMENTS

| | | | | |
|---|---|---|---|---|
| 5,505,956 | A * | 4/1996 | Kim | A61K 9/7053 424/448 |
| 6,383,511 | B1 * | 5/2002 | Cassel | A61K 31/245 424/449 |
| 2003/0082225 | A1 * | 5/2003 | Mason | A61K 9/7053 424/449 |
| 2004/0096491 | A1 | 5/2004 | Tateishi et al. | |
| 2004/0219196 | A1 | 11/2004 | Hart et al. | |
| 2004/0228802 | A1 * | 11/2004 | Chang | A61K 9/14 424/10.2 |
| 2007/0196452 | A1 | 8/2007 | Zhang et al. | |
| 2008/0003273 | A1 * | 1/2008 | Feldkamp | A61K 9/0014 424/448 |
| 2008/0318905 | A1 * | 12/2008 | Muhammad | A61P 19/02 540/487 |
| 2009/0246265 | A1 * | 10/2009 | Stinchcomb | A61K 9/7061 424/449 |
| 2010/0092544 | A1 * | 4/2010 | Okada | C09J 145/02 424/443 |
| 2010/0330383 | A1 * | 12/2010 | Nugent | C08L 29/04 428/520 |
| 2016/0367536 | A1 | 12/2016 | Kawakami | |
| 2017/0007550 | A1 | 1/2017 | Enscore et al. | |

FOREIGN PATENT DOCUMENTS

| | | |
|---|---|---|
| JP | 3-501386 | 3/1991 |
| JP | 2006-525316 A | 11/2006 |
| JP | 2009-519958 A | 5/2009 |
| JP | 2010-229045 A | 10/2010 |
| WO | WO 1989/011872 A1 | 12/1989 |
| WO | WO 2002/069942 A1 | 9/2002 |
| WO | WO 2003/103673 A1 | 12/2003 |
| WO | WO 2007/070695 | 6/2007 |
| WO | WO 2015/112563 A2 | 7/2015 |
| WO | WO 2015/133329 A1 | 9/2015 |

OTHER PUBLICATIONS

PCT International Search Report and Written Opinion, PCT/JP2017/010779, dated Sep. 25, 2018, in 11 pages.
Extended European Search Report, Applicatoin No. PCT/JP2017/010779, dated Oct. 15, 2019, in 7 pages.
Communication issued in corresponding European Patent Application No. 17770126.5 dated Mar. 4, 2021.
Office Action issued in corresponding Japanese Patent Application No. 2018-507290 dated Mar. 16, 2021.
China Pharmaceuticals, 24 (5): 87-88 (2015) (see concise explanation of relevance in Office Action of corresponding Chinese Patent Application No. 201780019826.4).

* cited by examiner

PATCH PREPARATIONS WITH ACCIDENTAL USE PREVENTION FEATURES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure relates to a patch preparation having features that prevent accidental use.

Description of the Related Art

Accidental use of pharmaceutical products including over-the-counter drugs and prescription drugs has been the primary cause of poisoning in children worldwide for many years. In particular, patch preparations can still contain a certain amount of active ingredient after being used or removed from the skin. These used preparations can sometimes adhere to another person's skin, by accident or intentionally, which can cause poisoning, and occasionally, death. In order to prevent accidental use due to the carelessness like this and/or intentional abuse, techniques to ensure safe disposal of used preparations were disclosed in WO 2003/103673.

SUMMARY

Problem to be Solved

An object of the present disclosure is to provide a patch preparation with a accidental use resistance feature that does not require a patient activation or performing a certain action after removal from the skin.

Means for Solving the Problems

As a result of intensive investigation, the present inventors found that the problem mentioned above can be solved by a patch preparation containing a solvent with a specific vapor pressure in its plaster, thus achieved the present object.

Non-limiting examples and embodiments of the present disclosure include the following (1) to (20):

(1) A patch preparation comprising a plaster disposed on a support, wherein the plaster comprises a solvent having a vapor pressure equal to or greater than 1 kPa at 20° C., and the amount of the solvent is about 2% to 35% by weight of the plaster.

(2) The patch preparation of item (1), wherein the amount of solvent is about 5% to about 25% by weight of the plaster.

(3) The patch preparation of item (1) or (2), wherein the solvent is selected from the group consisting of an acyclic or cyclic aliphatic hydrocarbon, an aliphatic alcohol, an esters, a ketones, an ether, an aromatic hydrocarbons, and water, and combinations thereof.

(4) The patch preparation of item (3), wherein the solvent is selected from the group consisting of n-hexane, n-heptane, cyclohexane, ethanol, isopropyl alcohol, isobutyl alcohol, 2-buthanol, isobutyl acetate, isopropyl acetate, ethyl acetate, acetone, methyl-ethyl-ketone, methyl-isobutyl-ketone, diethyl ether tetrahydrofuran, 1,4-dioxyane, benzene, xylene, and water, and combinations thereof.

(5) The patch preparation of any one of items (1) to (4), wherein the plaster further comprises a medicament.

(6) The patch preparation of item (5), wherein the medicament is selected from the group consisting of hypnosedative, stimulant, psychoneurotic agent, regional anesthetic, muscle relaxant, suxametonium, antiparkinsonian agent, antimigraine agent, anti-smoking drug, anti-allergic agent, anti-Alzheimer's agent, and opioid analgesic medication, and combinations thereof.

(7) The patch preparation of item (6), wherein the medicament comprises or is selected from the group consisting of one or more opioid analgesic medications selected from the group consisting of morphine, codeine, fentanyl, oxycodone, and hydromorphone, and combinations thereof.

(8) The patch preparation of any one of items (1) to (7), wherein the plaster further comprises a base material.

(9) The patch preparation of item (8), wherein the base material comprises an elastic polymer.

(10) The patch preparation of item (9), wherein the elastic polymer comprises an acrylic polymer, a rubber polymer, or a silicone-based polymer, or combinations thereof; or wherein the elastic polymer is selected from the group consisting of an acrylic polymer, a rubber polymer, and a silicone-based polymer.

(11) The patch preparation of any one of items (1) to (10), wherein the plaster further comprises one or more additives.

(12) The patch preparation of any one of items (1) to (11), wherein the support is a solvent permeable support.

(13) The patch preparation of any one of items (1) to (11), wherein the support is a solvent impermeable support.

(14) A patch preparation comprising a solvent permeable support, a first plaster, a solvent impermeable support, and a second plaster, wherein:
  the first plaster is disposed on the solvent permeable support;
  the solvent impermeable support is disposed on the first plaster;
  the second plaster is disposed on the solvent impermeable support, and the second plaster comprises a medicament; and
  the surface area of the first plaster is greater than the surface area of the solvent impermeable support, and the surface area of the solvent impermeable support is greater than or equal to the surface area of the second plaster.

(15) The patch preparation of item (14), wherein the first plaster does not contain a medicament.

(16) A method of preparing a patch preparation comprising:
  providing a support;
  providing a coating solution comprising a solvent and a polymer;
  disposing the coating solution on the support to form a plaster; and
  drying the plaster until the amount of the solvent is about 2% to 35% by weight of the plaster.

(17) The method of item (16), wherein the coating solution further comprises a medicament.

(18) The method of item (16) or (17), wherein the solvent has a vapor pressure equal to or greater than 1 kPa at 20° C.

(19) The patch preparation of any one of items (1) to (15) for percutaneous delivery of a medicament, wherein the patch preparation loses its adhesion when the plaster is exposed to air and the solvent concentration in the plaster decreases more than 50% or after the patch preparation is removed from skin.

(20) The patch preparation of any one of items (1) to (15) for percutaneous delivery of a medicament, wherein the patch preparation loses its adhesion partially or completely when the plaster is exposed to air for at least about 1 minute, 2 minutes, 3 minutes, 4 minutes, 5 minutes, 6 minutes, 7 minutes, 8 minutes, 9 minutes, 10 minutes, or a time frame defined by any of the two preceding values.

(21) A method of preventing or reducing the occurrence of accidental use or abuse of a patch preparation for percutaneous delivery of a medicament, comprising: providing a patch preparation of any one of items (1) to (15) to a subject in need thereof, wherein the patch preparation loses its adhesion when the plaster is exposed to air and the solvent concentration in the plaster decreases more than 50% or after the patch preparation is removed from skin.

(22) A method of preventing or reducing the occurrence of accidental use or abuse of a patch preparation for percutaneous delivery of a medicament, comprising: providing a patch preparation of any one of items (1) to (15) to a subject in need thereof, wherein the patch preparation loses its adhesion partially or completely when the plaster is exposed to air for at least about 1 minute, 2 minutes, 3 minutes, 4 minutes, 5 minutes, 6 minutes, 7 minutes, 8 minutes, 9 minutes, 10 minutes, or a time frame defined by any of the two preceding values.

DETAILED DESCRIPTION

Figure 1:
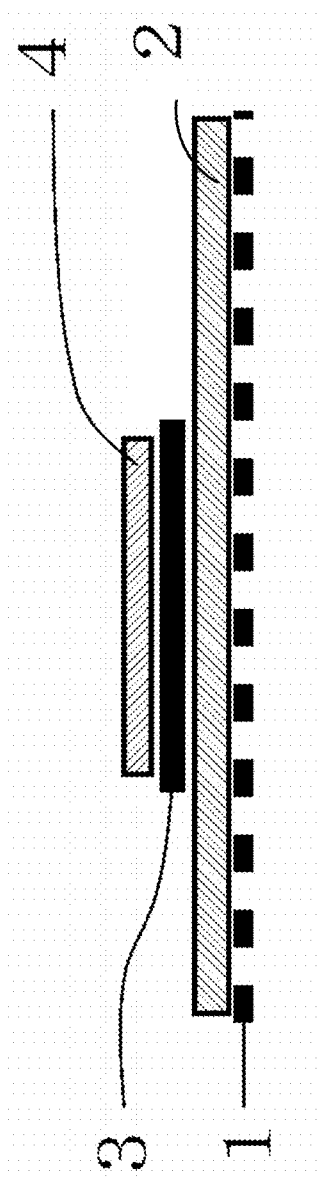
FIG. 1 shows a schematic cross-sectional view of an example of a multilayer patch preparation.

The patch preparation of the present disclosure comprises a support and one or more plasters. In some embodiments described herein, the plaster comprises a solvent, a base material, and does not comprise an active ingredient or medicament. In some other embodiments, the plaster described herein comprises an active ingredient or a medicament, a solvent, and a base material. In some embodiments, the patch preparation comprises both a medicament-free plaster and a medicament-containing plaster. In some embodiments, the plaster can also contain one or more additives.

Solvent

The solvent that is included in the plaster has a vapor pressure that is equal to or greater than 1 kPa at 20° C. The amount of the solvent in the plaster is about 2 wt % to about 35 wt % of the plaster. Some examples of useful solvent include, but not limited to, acyclic or cyclic aliphatic hydrocarbons such as n-hexane, n-heptane, and cyclohexane; an aliphatic alcohol such as ethanol, isopropyl alcohol, isobutyl alcohol, and 2-buthanol; esters such as isobutyl acetate, isopropyl acetate, and ethyl acetate; ketones such as acetone, methyl-ethyl-ketone, and methyl-isobutyl-ketone; ethers such as diethyl ether tetrahydrofuran and 1,4-dioxyane; aromatic hydrocarbons such as benzene and xylene; inorganic solvent such as water and buffer solutions; and combinations thereof.

The solvent with a vapor pressure that is equal to or greater than 1 kPa at 20° C. rapidly escapes from the plaster under the room temperature or at skin surface temperature (about 32° C.). Consequently, adhesiveness of the plaster is reduced or lost, and it prevents reapplication of the used patch preparation onto the skin. In some embodiments, the reduction in the amount of solvent in the patch can also lead to a reduction or a loss of skin permeability of the medicament that is dissolved in the solvent.

In some embodiments, the amount of the solvent with a vapor pressure that is equal to or greater than 1 kPa may be about 2% to about 35% by weight, about 3% to about 20% by weight, or about 4% to about 12% by weight relative to the total weight of the plaster. In some embodiment, the amount of the solvent may be about 5% to about 35%, about 10% to about 35%, about 12% to about 30%, or about 15% to about 28%, relative to the total weight of the partially dried plaster. In some embodiment, when the plaster contains no medicament and/or when base material is an acrylic polymer, the amount of the solvent may be about 2% to about 35%, about 4% to about 30%, about 5% to about 25% or about 5% to about 12% by weight, relative to the total weight of the plaster. If the amount of such solvent was too low, adhesiveness reducing effect may not be obtained. If the amount of such solvent was too high, the patch preparation may not be formed appropriately. As used herein, the term "plaster" refers to a component of a patch preparation that may be in the form of a plaster layer on a support. Plaster is formed by mixing a solvent with a base material, then the solvent is partially or substantially dried. Other components of a plaster may include, but not limited to one or more medicaments and/or additives or combinations thereof.

In some embodiments, the amount of solvent is maintained at a substantially fixed level starting from the post production packaging of the patch to the removal of the release film. In some embodiments, the amount of solvent decreases less than about 5%, about 3%, about 2% or about 1%. As used herein, the amount of the solvent in the patch at post production packaging is measured after the coating and drying process that forms the plaster, and not the amount of the solvent in the plaster solution that was initially coated onto the support during the plaster preparation.

In order to maintain the amount of solvent in the patch, some appropriate means, for example wrapping the patch in a wrapping material or enclosing the patch in a sealed packaging, can be employed. Before the patch application, the surface of the plaster is usually protected by a release film. In some embodiments, the release film may be impermeable to the solvent.

Base Material

The term "base material" as used herein, refers to a component of a plaster. In some embodiments, a base material may comprise a polymer. In some embodiments, the base material comprises an elastic polymer. Suitable elastic polymers may include, but not limited to acrylic polymers, rubber polymers, and silicone-based polymers. One or more synthetic rubber polymers such as styrene-isoprene-styrene block copolymer, styrene-butadiene-styrene block copolymer, polyisoprene, polyisobutylene, and polybutadiene may also be used, and in some instances are preferred. When a rubber polymer is used, the concentration of the rubber polymer may be about 3% to about 40% by weight, about 4% to about 30% by weight, about 5% to about 20%, or about 5% to about 12% by weight relative to total weight of the plaster. When an acrylic polymer is used, the concentration of the acrylic polymer may be about 15% to about 80% by weight, about 20% to 70% by weight, or about 30% to about 60% relative to total weight of the plaster.

Medicaments

The patch preparation of the present disclosure may include one or more medicament in the plaster. The medicament may include any active ingredient that is suitable for a patch preparation, and the type of medicament is not limiting. For example, the medicament may comprise or be selected from hypnosedative, stimulant, psychoneurotic agent, regional anesthetic, muscle relaxant suxametonium, antiparkinsonian agent, antimigraine agent, anti-smoking drug, anti-allergic agent, anti-Alzheimer's agent, or opioid analgesic medication. The medicament may include one or more opioid analgesic medications such as morphine, codeine, fentanyl, oxycodone, and hydromorphone, or combinations thereof. Since these medicaments can be abused, there is a high demand for accidental use prevention.

Additives

In some embodiments, the patch preparation may further comprise one or more additives. For example, the plaster may further contain an agent for preventing accidental ingestion. For example, substance having a strong bitter taste, such as denatonium benzoate, can be utilized. When concentration of denatonium benzoate is about 0.001% to about 0.1% by weight, or about 0.001% to about 0.01% by weight relative to total weight of the plaster, the patch preparation exhibits strong bitter taste in mouth and discourages ingestion by people (including children) and some animals.

Tackifiers

In some embodiments, the plaster may further contain one or more tackifiers. Rosin ester, hydrogenated rosin ester, maleate rosin, alicyclic saturated hydrocarbon resin, terpene resin, and polyolefin resin can be exemplified as the tackifiers. The concentration of the tackifier may be about 10% to about 40% by weight, about 20% to about 30% by weight, or about 22% to about 28% by weight relative to total weight of the plaster.

Percutaneous Absorption Accelerator

In some embodiments, the plaster may further comprise one or more organic solvents having percutaneous absorption accelerate effect. The organic solvent includes, for example, fatty acids, fatty alcohols, esters, and organic amine compounds. Examples of suitable fatty acids include capric acid, sorbic acid, levulinic acid, lauric acid, myristic acid, stearic acid, isostearic acid, and oleic acid. Examples of suitable fatty alcohols may include monovalent alcohol such as capryl alcohol, lauryl alcohol, myristyl alcohol, cetyl alcohol, stearyl alcohol, oleyl alcohol; and polyvalent alcohol such as propylene glycol, polyethylene glycol, and glycerin. Examples of suitable esters may include propylene carbonate, diethyl sebacate, isopropyl myristate, diisopropyl adipate, palmitic myristate, stearyl stearate, and $C_{5-12}$ medium-chain triglyceride. Examples of suitable organic amine compounds may include monoethanolamine, monoisopropanolamine, diethanolamine, diisopropanolamine, and triisopropanolamine.

In some embodiments, a solvent having a percutaneous permeation accelerate effect and a vapor pressure equal to or greater than 1 kPa at 20° C. is preferably chosen as the solvent in the plaster disclosed herein. For example, when oxycodone is an active pharmaceutical ingredient in the patch, ethyl acetate and/or n-heptane may be used as the solvent. When ethyl acetate and n-heptane are used in combination, the ratio between ethyl acetate and n-heptane may be, for example, 1:2 to 10:1. In embodiments where fentanyl is the medicament in a patch, any one of ethanol, isopropanol, or ethyl acetate may be used.

The plaster may also contain other additives such as a filler, an antioxidant agent, a pH adjuster, and perfume, or combinations thereof.

Support

The plaster is deposited or laminated on one of the surfaces of the support to form the patch preparation described herein. The support can be a support which is permeable to a solvent with a vapor pressure equal to or greater than about 1 kPa at 20° C. (i.e., "solvent permeable support"), or a support which is impermeable or substantially impermeable to the such solvent (i.e., "solvent impermeable support").

Solvent permeation rate of the solvent permeable support may be greater than 1 mg/l cm$^2$/24 hr, meaning more than 1 mg of solvent evaporates through 1 cm$^2$ of the support in 24 hours. Solvent permeation rate of the solvent impermeable support may be smaller than 0.5 mg/l cm$^2$/24 hr.

A solvent-permeable support may comprise or be selected from porous materials such as woven or non-woven cloth or porous sheet support. In some embodiments, the woven or non-woven cloth or sheet comprises resin such as polyester, polypropylene, polyurethane, or vinyl chloride, or combinations thereof; or pulp.

A solvent-impermeable support may comprise or be selected from a non-porous sheet or coated cloth or sheet. In some embodiments, the coated cloth or sheet is coated with a resin film comprising polyethylene terephthalate, polyamide, or vinyl chloride, or combinations thereof. In some further embodiments, the coated cloth or sheet comprises a woven or non-woven cloth coated with a resin coating material. The resin coating material may include, for example, polyethylene terephthalate (PET), or a resin material disclosed herein. The resin coating material may be any of the material form the resin film mentioned herein.

In some embodiments, the solvent-impermeable support may be or comprise a bilayer or multi-layer film. The bilayer film may be or comprise a laminated product of PET and polyethylene. The multi-layer film may comprise woven or non-oven cloth as an external layer. In one embodiment, the solvent-impermeable support is a multi-layer film comprising polyethylene film, PEP film and non-woven cloth made of PET. In a further embodiment, the arrangement of this multi-layer film is as follows: polyethylene film/PET film/non-woven cloth made of PET. When woven cloth or non-woven cloth is used as the most external layer (the layer on which plaster is directly disposed), fibers of the cloth are partially embedded in the plaster layer to fix the plaster onto the support.

When the support is a solvent-permeable support, the patch preparation may be wrapped with an appropriate wrapping material until just before applied on the skin surface, so as to prevent evaporation of the solvent from the plaster. The amount of the solvent with a vapor pressure equal to or greater than about 1 kPa at 20° C. is maintained in predetermined range until the release film is removed. Under this condition, the plaster has enough adhesiveness. Therefore, when it is applied on the skin surface, it adheres to the skin surface and the adhesion state is maintained.

During the adhesion to the skin, the solvent may evaporate through the solvent-permeable support, and is eliminated from the plaster. In some embodiments, the solvent may be partially or completely eliminated from the plaster within about 5 minutes, within about 10 minutes, within about 15 minutes or within about 30 minutes after the patch is removed from the wrapping materials. In some embodiments, even after the solvent has evaporated, the patch preparation continues to adhere to the skin. However, once the patch preparation is peeled off from the skin in the state that the solvent has evaporated from the plaster, the plaster loses or has a reduced adhesiveness. Therefore, the patch preparation does not re-adhere to the skin after it has been removed. The "state that the solvent has evaporated from the plaster" means that the amount of the solvent is less than about 30%, less than about 35%, less than about 40%, less than about 45%, less than about 50%, less than about 55%, less than about 60%, less than about 65%, less than about 70%, less than about 75%, or less than about 80% of the amount of solvent at the time of removing the release film, or in a range defined by any of the two preceding values.

In other words, once more than about 30%, about 35%, about 40%, about 45%, about 50%, about 55%, about 60%, about 65%, about 70%, about 75%, or about 80% of the solvent in the plaster has evaporated, the patch would no longer adhere to the skin. However, in some embodiments, if the patch was already on the skin, the patch will stay on the skin even if the solvent was evaporated, for example, through the solvent-permeable support. In these embodiments, the patch will lose its adhesion as soon as, or soon after, it is peeled off the skin.

In some embodiments, the patch preparation would lose or reduce its adhesion when the plaster is exposed to air for at least about 5 minutes, about 10 minutes, or about 15 minutes.

In some embodiments, when the support is the solvent-impermeable support, the patch preparation may be wrapped with an appropriate wrapping material until just before applying the patch on the skin surface, so as to prevent evaporation of the solvent from the plaster. The amount of the solvent in the plaster disposed on the solvent-impermeable support is kept constant until the release film is removed. Even after the application to the skin, the amount of the solvent is not substantially changed, because the plaster is covered with the solvent-impermeable support on one side, and attached to the skin surface on the other side. In certain instances, a certain amount of solvent may permeate through the skin. The plaster is warmed by body heat to almost the same as skin surface temperature (about 32° C.) after application, thus the solvent is rapidly evaporated from the plaster once the patch is removed from the skin. Consequently, adhesiveness of the plaster is lost or reduced quickly after the patch removal, and the patch does not re-adhere to the skin again.

In some embodiments, the permeability of an active ingredient or medicament through the skin may depend on the type of solvent it is dissolved in. In some embodiments that requires the solvent to carry the active ingredient or medicament through the skin, an active ingredient/medicament may have difficulty in penetrating through the skin after the solvent has evaporated following the removal of the patch.

In some embodiments, the solvent-permeable support and the solvent-impermeable support can be used in combination. In this case, the patch preparation can be a laminated body comprising a first and a second plaster, and a first and a second support. The first support is a solvent-permeable support, and the second support is a solvent-impermeable support. In some embodiments, the first plaster does not contain any medicament, and second plaster contains one or more medicaments. In some embodiments, the first support, the first plaster, the second support, and the second plaster are laminated in this order, and the second plaster is configured to adhere to the skin. The surface areas of the patch layers satisfy the following formula:

first plaster>second support≥second plaster

In other words, the surface area of the first plaster is greater than the surface area of the solvent-impermeable support, and the surface area of the solvent-impermeable support is greater or equal to the surface area of the second plaster.

In some embodiments, their surface areas satisfy the following formula:

first support≥first plaster>second support≥second plaster

In some embodiments, the patch further has a release layer on the second plaster.

An Example of patch preparation as described herein is further illustrated in FIG. 1. In FIG. 1, element 1 illustrates a solvent-permeable support, element 3 illustrates a solvent-impermeable support, elements 2 and 4 illustrate a first plaster and a second plaster respectively. The first plaster (2) is disposed on the solvent-permeable support (1), the solvent-impermeable support (3) is disposed on the first plaster (2), and the second plaster (4) is disposed on the solvent-impermeable support (3). The second plaster (4) comprises a medicament.

In the example described in FIG. 1, the first support plays a role in attaching and fixing the patch preparation on a skin surface. The second plaster plays a role in storing a medicament, and releasing the medicament after application of the patch to the skin. Therefore, the surface area of the first support is preferably larger compared to the surface area of the second support and the second plaster. In some embodiments, the surface area of the second support may be less than about 75%, about 70%, about 65%, about 60%, about 55%, about 50%, about 45%, about 40%, about 35%, or about 30% of that of the first support, or in a range defined by any of the two preceding values. In some embodiments, the second plaster is not especially required to have adhesiveness. In some embodiments, the second plaster does not have enough adhesiveness to keep adhesion to the skin surface by itself.

As described herein, the first plaster has enough adhesiveness to keep adhesion to skin after application of the patch. During application, the solvent as describe herein evaporates, and may be partially or completely eliminated from the plaster within about 5 minutes, within about 10 minutes, within about 15 minutes or within about 30 minutes after the application. Thus, once the patch preparation is removed from skin surface, it does not exhibit adhesiveness. Therefore, the patch preparation does not adhere to the skin again following the removal.

However, once the patch has been applied to the skin, it continues to adhere to the skin surface until it is peeled off. In some embodiments, the patch continues to adhere to the skin after more than about 30 minutes, about 8 hours, about 12 hours or about 24 hours have passed. In some embodiments, the patch continues to adhere to the skin after the solvent has evaporated from the plaster. The second plaster contains a medicament dissolved in the solvent, and the medicament exhibits percutaneous permeability. However, once the second plaster is removed from skin surface, the solvent is rapidly eliminated from the plaster. Consequently, the percutaneous permeability of the medicament is remarkably decreased when it is put in contact with the skin again.

Methods of Making the Patch Preparation

In some embodiments, the patch preparation is made by disposing a coating liquid or coating solution on a support to form a plaster on the support, and drying the plaster to form a sticky or adhesion surface.

A solution containing a base material is provided by dissolving one or more polymers in a first solvent. In some embodiments, the solution containing the base material is used as the coating solution. In some embodiments, an active agent solution and the base material solution are combined to form the coating solution. In some embodiments, the solvent used for preparing a base material solution is the same as the solvent used for preparing the active agent solution, for example, heptane, ethyl acetate or a combination thereof. In other embodiments, the solvent used for preparing a base material solution may be different from the solvent used for preparing the active agent solution, as long as the vapor pressure of the solvent is greater than 1 kPa.

The active agent/medicament solution is provided by adding the active agent/medicament to a second solvent and mixing to dissolve the active agent/medicament. The first and the second solvent described herein may be the same, or may be different. In some embodiments, the first and the second solvent may comprise a solvent described herein, for example, ethanol, ethyl acetate, propanol, isopropanol, n-propyl acetate, isopropyl acetate, 1-butanol, 2-butanol, t-butyl alcohol, n-butyl acetate, isobutyl acetate, n-hexane, 2-hexane, 1-hexanol, 2-hexanol, n-heptane, 1-heptanol, cyclohexane, tetrahydrofuran, acetone, methyl-ethyl-ketone, methyl-isobutyl-ketone, diethyl ether, 1,4-dioxyane, benzene, xylene, or water, or combinations thereof. In some embodiments, may also include a third solvent that can serve as a percutaneous absorption accelerator described herein. In some embodiments, one or more additives may also be added to the active agent solution or the base material solution or both, such as filler, an antioxidant agent, a pH adjuster, and perfume.

The coating solution is disposed or coated onto a support to form a plaster. The plaster is then dried until the amount of solvent remained in the plaster is within the selected range described herein. For example, the plaster is dried until the amount of the solvent is about 2% to about 30% by weight of the plaster.

A release film is applied to the exposed plaster surface once the desired solvent concentration has been reach. And the patch preparation may be packaged.

EXAMPLES

The present disclosure is described in detail with the following examples. The examples below are non-limiting and are merely representative of various aspects of the disclosure.

Patch Preparations 1-A and 1-B Containing Oxycodone

Patch preparations containing oxycodone with the composition shown in Table 1 were prepared. Potassium hydrate, levulinic acid, and glycerin were heated and mixed. After they were dissolved, sodium acid sulfite was added and mixed to form a mixture. Oleic acid, denatonium benzoate, diisopropanolamine, propylene carbonate, and propyl gallate were then added to the mixture, and the mixture was heated and stirred. Subsequently, oxycodone hydrochloride was added to the mixture, and the mixture was heated and mixed again to yield an oxycodone solution. Separately, terpene resin, styrene-isoprene-styrene block copolymer, light anhydrous silicic acid, ethyl acetate, and heptane were mixed together to yield a viscous elastomer liquid. The oxycodone solution and the elastomer liquid were mixed to yield a coating liquid. The coating liquid was coated on a PET liner treated with silicon treatment liquid, and dried until both concentrations of ethyl acetate and heptane relative to total weight of the plaster achieved about 10% by weight. It was laminated on one of the surfaces of the PET film (support). Thus, a patch preparation 1-A comprising a release liner was obtained.

Patch preparation 1-B was prepared the same way preparation 1-A was prepared, then a release liner was peeled off from the patch preparation 1-B, leaving one side of the plaster exposed to air at room temperature for about an hour to allow evaporation of ethyl acetate and heptane from the plaster.

After one hour at room temperature, the patch preparation 1-A exhibited tackiness when evaluators touched the plaster with their gloved hand. By contrast, the patch preparation 1-B didn't exhibit tackiness when the evaluators touched the plaster with their gloved hand.

Patch Preparations 2-A and 2-B Containing Oxycodone

Patch preparations 2-A and 2-B were prepared following the same procedure described above for the patch preparation 1-A and 1-B, except that the amount of the components used for the patch preparation 1-A and 1-B was changed as shown in Tale 1, and the concentrations of ethyl acetate and heptane after dried were adjusted to 5% respectively.

The release liner of the patch preparation 2-B was peeled off, leaving one side of the plaster exposed to air at room temperature for one hour, allowing evaporation of ethyl acetate and heptane from the plaster.

After one hour, the patch preparation 2-A exhibited tackiness when evaluators touched the plaster with their gloved hand. By contrast, the patch preparation 2-B didn't exhibit tackiness when the evaluators touched the plaster with their gloved hand.

In Vitro Evaluation of Percutaneous Permeability

As to the patch preparations 1-A through 2-B, percutaneous permeability of oxycodone was evaluated using Franz static diffusion cells. Pig skin was used for the experiment. The amount of the cumulative skin permeation at each sampling point (2 hr, 4 hr, 6 hr, and 8 hr) is shown in Table 2. As is clear from Table 2, the patch preparations 1-B and 2-B exhibited significantly lower cumulative skin permeation at each sampling point compared with those of the patch preparations 1-A and 2-A.

TABLE 1

|  | 1-A | 1-B | 2-A | 2-B |
| --- | --- | --- | --- | --- |
| Oxycodone hydrochloride•3H$_2$O | 18.64 | 18.64 | 19.62 | 19.62 |
| ethyl acetate | 372.88 | 372.88 | 392.39 | 392.39 |
| heptane | 124.29 | 124.29 | 130.80 | 130.80 |
| glycerin | 15.54 | 15.54 | 16.35 | 16.35 |
| oleic acid | 24.86 | 24.86 | 26.16 | 26.16 |
| levulinic acid | 6.21 | 6.21 | 6.54 | 6.54 |
| diisopropanolamine | 4.35 | 4.35 | 4.58 | 4.58 |
| propylene carbonate | 31.07 | 31.07 | 32.70 | 32.70 |
| terpene resin | 273.44 | 273.44 | 261.59 | 261.59 |
| SIS copolymer | 87.01 | 87.01 | 65.40 | 65.40 |
| potassium hydrate | 3.42 | 3.42 | 3.60 | 3.60 |
| light anhydrous silicic acid | 37.29 | 37.29 | 39.24 | 39.24 |

TABLE 1-continued

|  |  | 1-A | 1-B | 2-A | 2-B |
|---|---|---|---|---|---|
| denatonium benzoate |  | 0.062 | 0.062 | 0.065 | 0.065 |
| sodium acid sulfite |  | 0.62 | 0.62 | 0.65 | 0.65 |
| propyl gallate |  | 0.31 | 0.31 | 0.33 | 0.33 |
| total |  | 1000 | 1000 | 1000 | 1000 |
| ethyl acetate content in the plaster |  | 10% | 10% | 5% | 5% |
| heptane content in the plaster |  | 10% | 10% | 5% | 5% |
| tack strength |  | ○ | X | ○ | X |
| cumulative skin permeation amount ($\mu g/cm^2$) | 2 hr | 6.90 | 0.00 | 2.10 | 0.80 |
|  | 4 hr | 16.50 | 1.10 | 12.50 | 5.20 |
|  | 6 hr | 29.00 | 4.30 | 27.60 | 12.20 |
|  | 8 hr | 42.90 | 9.90 | 44.90 | 21.30 |

○: felt tackiness when touch the adhesive layer with a gloved hand
X: did not feel tackiness when touch the adhesive layer with a gloved hand
SIS copolymer: styrene-isoprene-styrene copolymer Patch Preparations 3 and 4 Containing Oxycodone Patch preparations 3 and 4 were prepared following the same procedure described above for the patch preparation 1-A, except that the components with the amount shown in Table 2 were used to prepare the patch preparations 3 and 4, and a solvent permeable woven cloth was used instead of a PET liner. Each of the patch preparations 3 and 4 is applied to the skin for one hour at room temperature, and then is peeled off the skin. After leaving the patches at ambient temperature for about 30 minutes, the patch preparations 3 and 4 are then reapplied to the skin again. However, it is difficult for the patch preparations 3 and 4 to be re-adhered to the skin. This demonstrates that the safety feature of the patch formulation works as intended.

Patch Preparation 5 Containing Oxycodone

Patch preparation 5 was prepared following the same procedure described above for the patch preparation 1-A, except that the components shown in Table 2 were used to prepare the patch preparation 5. The patch preparation 5 is applied to the skin for 30 minutes at room temperature. The concentration level of the solvent in the plaster of the patch preparation 5 is maintained while it is adhered to the skin. 30 minutes after the patch preparation 5 is peeled off from the skin, the patch preparation 5 is applied to the skin again. However, the patch preparation 5 does not adhere to the skin since the solvent is rapidly eliminated from the plaster soon after the patch preparation 5 is peeled off from the skin.

TABLE 2

|  | 3 | 4 | 5 |
|---|---|---|---|
| Oxycodone hydrochloride•$3H_2O$ | 21.6 | 21.2 | 18.4 |
| ethyl acetate | 375.3 | 367.3 | 371.6 |
| heptane | 125.1 | 122.4 | 185.8 |
| glycerin | 0.0 | 15.3 | 13.3 |
| oleic acid | 25.0 | 24.5 | 21.2 |
| levulinic acid |  | 6.1 | 5.3 |
| diisoproopanolamine | 4.4 | 4.3 | 3.7 |
| propylene carbonate | 31.3 | 30.6 | 26.5 |
| medium-chain triglyceride |  | 30.6 |  |
| oleyl alcohol | 31.3 |  |  |
| terpene resin | 250.2 | 244.8 | 254.8 |
| SIS copolymer | 93.8 | 91.8 | 63.7 |

TABLE 2-continued

|  | 3 | 4 | 5 |
|---|---|---|---|
| potassium hydrate | 3.4 | 3.4 | 2.9 |
| light ahydrous silicic acid | 37.5 | 36.7 | 31.9 |
| denatonium benzoate | 0.0626 | 0.0612 | 0.0531 |
| sodium acid sulfite |  |  | 0.53 |
| propyl gallate | 0.31 | 0.31 | 0.27 |
| sodium pyrosulfite | 0.63 | 0.61 |  |
| total | 1000 | 1000 | 1000 |
| ethyl acetate content in the plaster | 8% | 8% | 3% |
| heptane content in the plaster | 3% | 3% | 4% |

Patch Preparation 6 Containing Oxycodone

Figure 2:
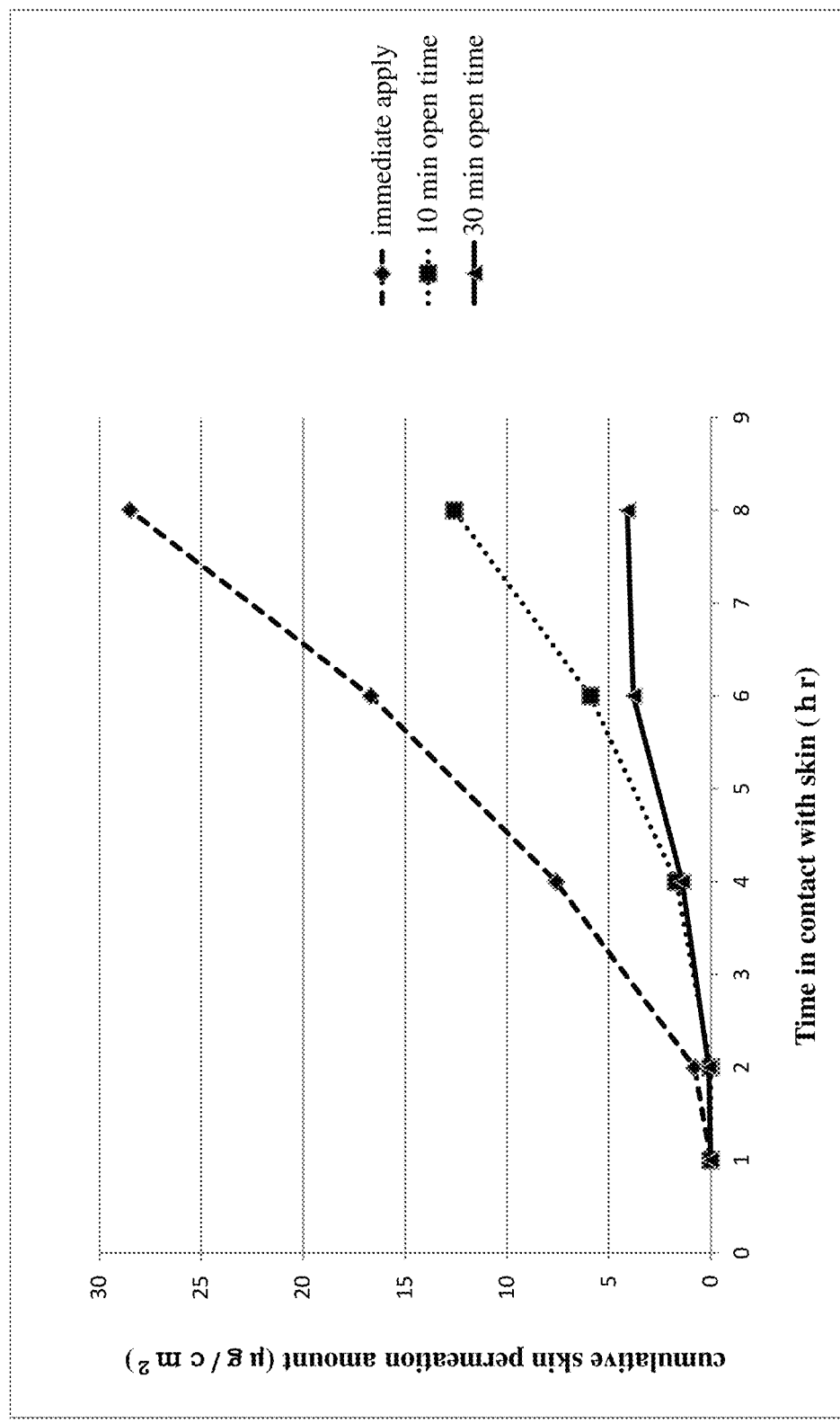
FIG. 2 shows the percutaneous permeability of Oxycodone of the patch preparation 6 evaluated by using Franz static diffusion cells at each sampling point (1 hr, 2 hr, 4 hr, 6 hr, and 8 hr).

Patch preparation 6 was prepared following the same procedure described above for the patch preparation 1-A, except that the amount of the components as shown in Table 3 were used for the patch preparation 6. The percutaneous permeability of oxycodone of the patch preparation 6 was evaluated using Franz static diffusion cells. Pig skin was used for the experiment. The amount of the cumulative skin permeation at each sampling point (1 hr, 2 hr, 4 hr, 6 hr, and 8 hr) is shown in Table 4 and FIG. 2.

Separately from the evaluation above, the release liner was peeled off from the patch preparation 6, and one side of the plaster of the patch preparation 6 was exposed to air. The patch preparation 6 was left for 10 minutes or 30 minutes under room temperature for ethyl acetate and heptane to evaporate from the plaster. After that, the percutaneous permeability of Oxycodone of the patch preparation 6 was evaluated using Franz static diffusion cells with pig skin. The amount of the cumulative skin permeation at each sampling point (1 hr, 2 hr, 4 hr, 6 hr, and 8 hr) is shown in Table 4 and FIG. 2. As is clear from FIG. 2, the cumulative skin permeation of the patch preparation 6 applied after 10 minutes or 30 minutes exposure to air was significantly lower than that of the patch preparation 6 applied to the skin immediately.

TABLE 3

| Patch Preparation 6 | Amount in the plaster (%) |
|---|---|
| oxycodone hydrochloride $3H_2O$ | 3.016 |
| ethyl acetate | 16.0 |
| heptane | 7.0 |
| glycerin | 2.178 |
| oleic acid | 3.485 |
| levulinic acid | 0.871 |
| diisopropanolamine | 0.610 |
| propylene carbonate | 4.357 |
| polyisobutylene | 1.743 |
| SIS-copolymer | 47.923 |
| terpene resin | 9.585 |
| potassium hydrate | 0.497 |
| light anhydrous silicic acid | 2.614 |
| denatonium benzoate | 0.009 |
| sodium acid sulfite | 0.087 |
| propyl gallate | 0.044 |
| total | 100.02 |

TABLE 4

| Patch Preparation 6 | | 1 hr | 2 hr | 4 hr | 6 hr | 8 hr |
|---|---|---|---|---|---|---|
| cumulative skin permeation amount (μg/cm²) | immediate apply | 0 | 0.8 | 7.6 | 16.7 | 28.5 |
| | 10 min open time | 0 | 0 | 1.7 | 5.9 | 12.6 |
| | 30 min open time | 0 | 0.1 | 1.4 | 3.8 | 4.1 |

Patch Preparation 7 Containing Fentanyl

Patch preparation 7 was prepared following the same procedure as described above for the patch preparation 1-A, except that Fentanyl was used as an active ingredient instead of Oxycodone hydrochloride, and the components with the amounts shown in Table 5 were used to prepare the patch preparation 7. In Table 5, the term "charged amount" refers to the amount of the components used to prepare the coating solution, and the term "amount after dried" refers to the amount of the components after some solvent has evaporated to form the plaster. The percutaneous permeability of Fentanyl of the patch preparation 7 was evaluated using Franz static diffusion cells. Pig skin was used for the experiment. The amount of the cumulative skin permeation at each sampling point (2 hr, 4 hr, 6 hr, 8 hr, and 24 hr) is shown in Table 6.

Figure 3:
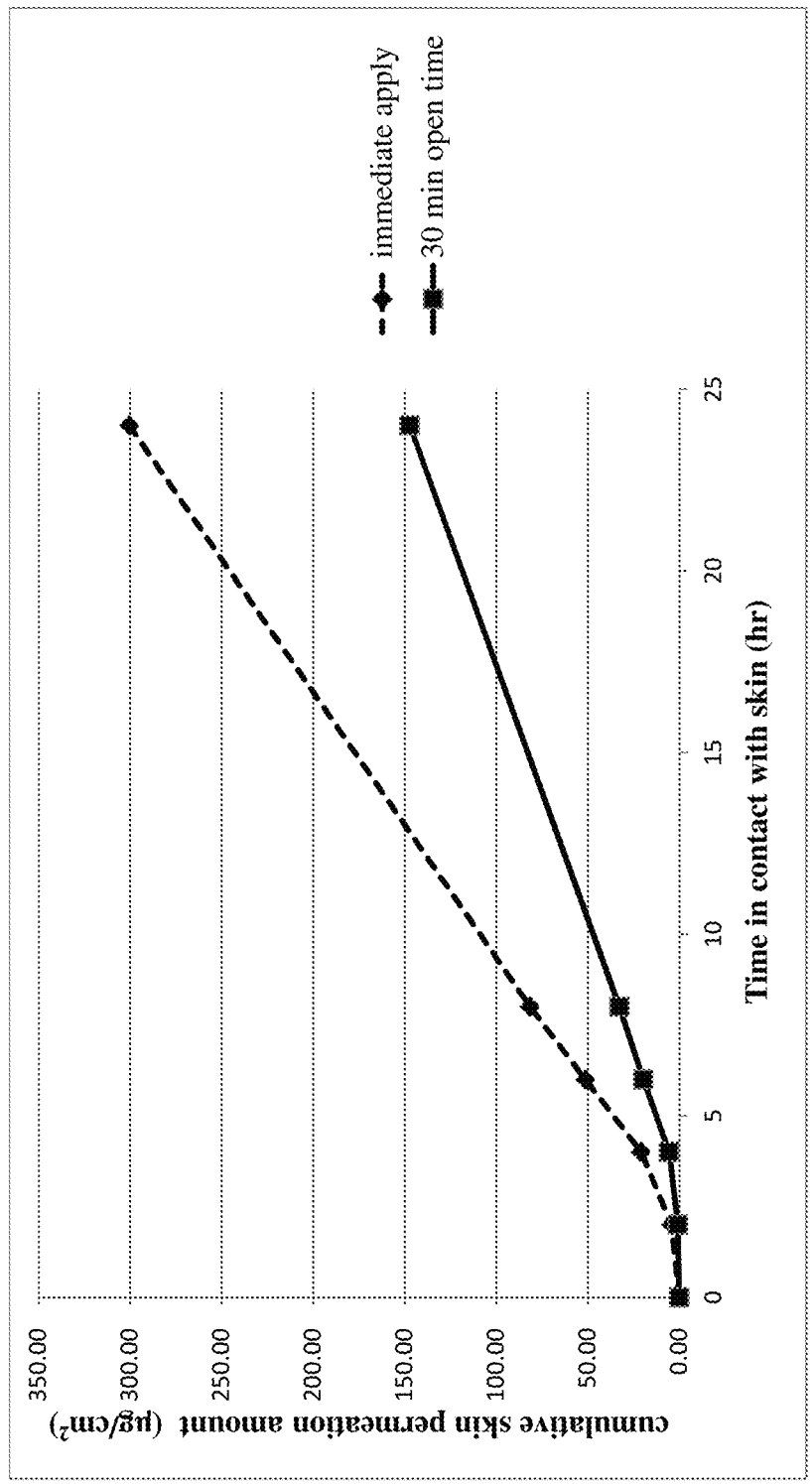
FIG. 3 shows the percutaneous permeability of Fentanyl of the patch preparation 7 evaluated by using Franz static diffusion cells at each sampling point (2 hr, 4 hr, 6 hr, 8 hr, and 24 hr).

Separately from the evaluation above, the release liner was peeled off from the patch preparation 7, allowing one side of the plaster of the patch preparation 7 to be exposed to air. The patch preparation 7 was left for 30 minutes at room temperature for ethyl acetate and heptane to evaporate from the plaster. After that, the percutaneous permeability of Fentanyl of the patch preparation 7 was evaluated using Franz static diffusion cells with pig skin. The amount of the cumulative skin permeation at each sampling point (2 hr, 4 hr, 6 hr, 8 hr, and 24 hr) is shown in Table 6 and FIG. 3. As is clear from FIG. 3, the cumulative skin permeation of the patch preparation 7 applied after 30 minutes exposure to air was significantly lower than that of the patch preparation 7 applied immediately.

TABLE 5

| Patch Preparation 7 | Charged amount (%) | Amount after dried (%) |
|---|---|---|
| fentanyl | 8.00 | 8.09 |
| ethyl acetate | 91.620 | 14.09 |
| heptane | 36.00 | 9.05 |
| polyisobutylene | 1.98 | 2.00 |
| SIS copolymer | 55.00 | 55.60 |
| terpene resin | 11.00 | 11.12 |
| propyl gallate | 0.05 | 0.05 |
| total | 203.65 | 100.00 |

TABLE 6

| Patch Preparation 7 | | 0 hr | 2 hr | 4 hr | 6 hr | 8 hr | 24 hr |
|---|---|---|---|---|---|---|---|
| Cumulative skin permeation (μg/cm²) | immediate apply | 0.00 | 4.20 | 20.76 | 51.26 | 81.50 | 300.39 |
| | 30 min open time | 0.00 | 0.71 | 5.50 | 19.54 | 32.66 | 147.27 |

Patch Preparation 8 Containing Hydromorphone

Figure 4:
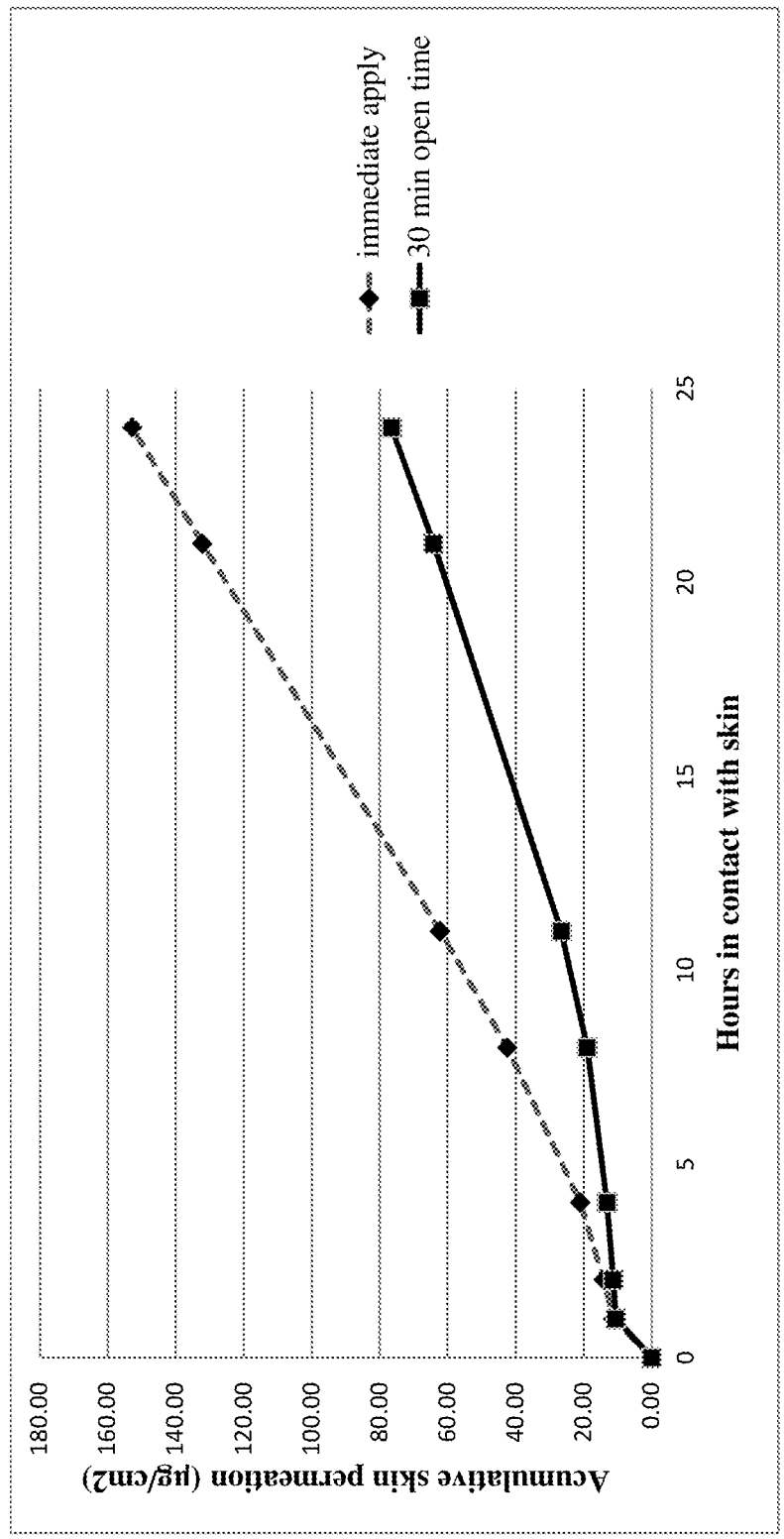
FIG. 4 shows the percutaneous permeability of Hydromorphone of the patch preparation 8 evaluated by using Franz static diffusion cells at each sampling point (1 hr, 2 hr, 4 hr, 8 hr, 11 hr, 21 hr, and 24 hr).

Patch preparation 8 was prepared following the same procedure described above for the patch preparation 1-A, except that Hydromorphone hydrochloride was used as an active ingredient instead of Oxycodone hydrochloride, and the components with the amount shown in Table 7 were used to prepare the patch preparation 8. In Table 7, the term "charged amount" refers to the amount of the components used to prepare the coating solution, and the term "amount after dried" refers to the amount of the components after some solvent has evaporated to form the plaster, and the term "amount after 30 min" refers to the amount of the components after 30 minute exposure to air. The percutaneous permeability of Hydromorphone of the patch preparation 8 was evaluated using Franz static diffusion cells. Pig skin was used for the experiment. The amount of the cumulative skin permeation at each sampling point (1 hr, 2 hr, 4 hr, 8 hr, 11 hr, 21 hr, and 24 hr) is shown in Table 8 and FIG. 4.

Separately from the evaluation above, the release liner was peeled off from the patch preparation 8, and one side of the plaster of the patch preparation 8 was exposed to air. The patch preparation 8 was left in the air for 30 minutes at room temperature. Following the 30-minute exposure, the patch preparation 8 was contacted to the pig skin and the percutaneous permeability of Hydromorphone of the patch preparation 8 was evaluated using Franz static diffusion cells. The amount of the cumulative skin permeation at each sampling point (1 hr, 2 hr, 4 hr, 8 hr, 11 hr, 21 hr, and 24 hr) is shown in Table 8 and FIG. 4. As is clear from FIG. 4, the cumulative skin permeation of the patch preparation 8 applied after 30 minutes exposure to air was significantly lower than that of the patch preparation 8 applied immediately.

TABLE 7

| Patch Preparation 8 | Charged amount (%) | Amount after dried (%) | Amount after 30 min (%) |
|---|---|---|---|
| hydromorphone hydrochloride | 3.00 | 2.83 | 2.59 |
| ethyl acetate | 75.00 | 17.89 | 0.52 |
| heptane | 5.00 | 0.98 | 0.27 |
| oleic acid | 2.00 | 1.89 | 1.73 |
| diisopropanolamine | 1.00 | 0.94 | 0.86 |
| glyceryl monostearate | 0.50 | 0.47 | 0.43 |
| HCO-40 | 1.50 | 1.42 | 1.29 |
| MCT | 2.00 | 1.89 | 1.73 |
| isopropyl mrystate | 1.00 | 0.94 | 0.86 |
| diethyl sebacate | 1.00 | 0.94 | 0.86 |
| glycerine | 4.00 | 3.78 | 3.45 |
| 1,3-butylene glycol | 4.00 | 3.78 | 3.45 |
| oleyl alcohol | 6.00 | 5.66 | 5.18 |
| terpene resin | 10.00 | 9.44 | 8.63 |
| SIS copolymer | 44.00 | 41.53 | 37.95 |
| poly isobutylene | 2.00 | 1.89 | 1.73 |
| light anhydrous silicic acid | 3.00 | 2.83 | 2.59 |
| denatonium benzoate | 0.01 | 0.01 | 0.14 |
| sodium acid sulfite | 0.20 | 0.19 | 0.17 |
| propyl gallate | 0.50 | 0.47 | 0.43 |
| BHT | 0.25 | 0.24 | 0.21 |
| total | 165.96 | 100.00 | 75.09 |

HCO-40: PEG-40 Hydrogenated Castor Oil
MCT: Medium-chain triglycerides
BHT: Butylated hydroxytoluene

TABLE 8

| Accumulative permeation (μg/cm²) | | 0 hr | 1 hr | 2 hr | 4 hr | 8 hr | 11 hr | 21 hr | 24 hr |
|---|---|---|---|---|---|---|---|---|---|
| Immediate apply | Mean. | 0.00 | 11.24 | 14.10 | 21.01 | 42.45 | 62.20 | 132.16 | 152.84 |
| | S.D. | 0.00 | 2.55 | 1.68 | 3.30 | 13.55 | 21.77 | 41.95 | 45.59 |
| 30 min open time | Mean. | 0.00 | 10.58 | 11.31 | 13.14 | 18.99 | 26.59 | 64.19 | 76.56 |
| | S.D. | 0.00 | 1.62 | 1.24 | 0.37 | 3.88 | 9.36 | 32.49 | 38.06 |

Patch Preparation 9

An appropriate amount of ethyl acetate was added to a 6:1 (by weight) mixture of styrene-isoprene-styrene block copolymer and terpene resin to form a coating liquid with a proper consistency for coating application. The coating liquid was coated onto a siliconized PET liner, and dried until ethyl acetate concentration in the plaster achieved 10% by weight to form a plaster with a PET liner on one surface. The plaster was then laminated onto a woven cloth (solvent-permeable support) to produce patch preparation 9. The obtained preparation was adhered to human skin surface. After 30 minutes of the adhesion, the patch preparation 9 was removed. Though the peeling stress was not small, the plaster after removal didn't exhibit adhesiveness and couldn't be re-adhered to the skin surface.

Patch Preparations 10-1 and 10-2 Containing No Active Ingredient

Ethyl acetate and heptane were added to a 1:1 (by weight) mixture of acrylic resin (DURO TAK) and terpene resin to form a coating liquid. The coating liquid was coated onto a siliconized PET liner, and dried until amount of each ingredient achieved a ratio as shown in Table 9. The plaster was laminated onto a woven cloth (solvent permeable support) to produce patch preparation 10-1. Patch preparation 10-2 was prepared following the same procedure of patch preparation 10-1, except that denatonium benzoate was further added. The obtained preparations 10-1 and 10-2 were adhered to human skin surface. After 30 minutes of the adhesion, the patch preparations were removed. Though the peeling stress was not small, the plaster after removal didn't exhibit adhesiveness and couldn't be re-adhered to the skin surface.

TABLE 9

| | 10-1 | 10-2 |
|---|---|---|
| acrylic resin | 47 | 47 |
| terpen resin | 47 | 47 |
| ethyl acetate | 3 | 3 |
| heptane | 3 | 2.99 |
| denatonium benzoate | | 0.01 |
| total | 100 | 100 |

What is claimed is:

1. A patch preparation comprising a plaster disposed on a support, wherein
the plaster comprises a base material, a medicament, one or more additives, and a solvent comprising a combination of ethyl acetate and n-heptane, and
an amount of the solvent is 15% to 35% by weight of the plaster,
an amount of n-heptane is 10% to 28% by weight of the plaster, and
the base material is selected from a rubber polymer or a combination of a rubber polymer and an acrylic polymer; wherein the patch preparation exhibited adhesion to skin immediately after preparing and no adhesion to skin after 1 hour of exposure to air following the preparation of the patch.

2. The patch preparation of claim 1, wherein the medicament comprises one or more compound selected from the group consisting of morphine, codeine, fentanyl, oxycodone, and hydromorphone, and combinations thereof.

3. The patch preparation of claim 1, wherein the medicament comprises fentanyl or oxycodone.

4. The patch preparation of claim 1, wherein the support is a solvent impermeable support.

5. The patch preparation of claim 1, wherein the support is a solvent permeable support.

6. The patch preparation of claim 1, wherein the one or more additives include denatonium benzoate.

7. The patch preparation of claim 1, further comprising one or more tackifiers selected from the group consisting of rosin ester, hydrogenated rosin ester, maleate rosin, alicyclic saturated hydrocarbon resin, terpene resin, and polyolefin resin.

8. The patch preparation of claim 1, further comprising one or more percutaneous absorption accelerators selected from fatty acids, fatty alcohols, esters, and organic amine compounds.

9. The patch preparation of claim 8, wherein the fatty acids are selected from the group consisting of capric acid, sorbic acid, levulinic acid, lauric acid, myristic acid, stearic acid, isostearic acid, and oleic acid.

10. The patch preparation of claim 8, wherein the fatty alcohols are selected from the group consisting of capryl alcohol, lauryl alcohol, myristyl alcohol, cetyl alcohol, stearyl alcohol, oleyl alcohol, propylene glycol, polyethylene glycol, and glycerin.

11. The patch preparation of claim 8, wherein the esters are selected from the group consisting of propylene carbonate, diethyl sebacate, isopropyl myristate, diisopropyl adipate, palmitic myristate, stearyl stearate, and C5-12 medium-chain triglyceride.

12. The patch preparation of claim 8, wherein the organic amine compounds are selected from the group consisting of monoethanolamine, monoisopropanolamine, diethanolamine, diisopropanolamine, and triethanolamine, triisopropanolamine.

13. The patch preparation of claim 5, wherein the solvent-permeable support comprises a woven or non-woven cloth including a resin selected from the group consisting of polyester, polypropylene, polyurethane, or vinyl chloride, or combinations thereof; or pulp.

14. The patch preparation of claim 4, wherein the solvent-impermeable support comprises coated cloth or sheet and is coated with a resin film comprising polyethylene terephthalate, polyamide, or vinyl chloride, or combinations thereof.

15. The patch preparation of claim 1, wherein the base material is a rubber polymer.

16. The patch preparation of claim 1, wherein the base material is a combination of a rubber polymer and an acrylic polymer.

* * * * *